United States Patent
Löbbert et al.

(10) Patent No.: US 10,436,738 B2
(45) Date of Patent: Oct. 8, 2019

(54) MEMBRANE AND METHOD OF MANUFACTURE

(71) Applicant: Endress+Hauser Conducta GmbH+Co. KG, Gerlingen (DE)

(72) Inventors: Andreas Löbbert, Waldheim (DE); Alexander Hörig, Geringswalde (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 189 days.

(21) Appl. No.: 15/384,799

(22) Filed: Dec. 20, 2016

(65) Prior Publication Data
US 2017/0176375 A1 Jun. 22, 2017

(30) Foreign Application Priority Data
Dec. 21, 2015 (DE) .................. 10 2015 122 463

(51) Int. Cl.
| | |
|---|---|
| G01N 27/40 | (2006.01) |
| B05D 3/06 | (2006.01) |
| B05D 3/14 | (2006.01) |
| G01N 21/77 | (2006.01) |
| G01N 21/64 | (2006.01) |

(52) U.S. Cl.
CPC .......... *G01N 27/40* (2013.01); *B05D 3/065* (2013.01); *B05D 3/148* (2013.01); *G01N 21/77* (2013.01); *G01N 2021/6432* (2013.01); *G01N 2021/775* (2013.01); *G01N 2021/7786* (2013.01)

(58) Field of Classification Search
CPC .............. G01N 27/40; G01N 21/77; G01N 2021/7786; G01N 2021/6432; G01N 2021/775; B05D 3/148; B05D 3/065
See application file for complete search history.

(56) References Cited

U.S. PATENT DOCUMENTS

| | | | |
|---|---|---|---|
| 3,686,091 A | 8/1972 | Sawa et al. | |
| 4,484,987 A | 11/1984 | Gough | |
| 2007/0131611 A1* | 6/2007 | Peng ................. | B01D 67/0088 210/500.27 |
| 2013/0211219 A1 | 8/2013 | Coppeta et al. | |
| 2014/0311905 A1 | 10/2014 | Stetter et al. | |

(Continued)

FOREIGN PATENT DOCUMENTS

| | | |
|---|---|---|
| CN | 101184851 A | 5/2008 |
| CN | 101511458 A | 8/2009 |

(Continued)

OTHER PUBLICATIONS

Search Report for German Patent Application No. 10 2015 122 463.1, German Patent Office, dated Nov. 17, 2016, 8 pp.

*Primary Examiner* — Dennis White
(74) *Attorney, Agent, or Firm* — Kelly J. Smith; PatServe

(57) ABSTRACT

The present disclosure concerns a membrane for a sensor, such as an opto-chemical or electrochemical sensor, including a polymer layer, for example, one featuring pores or openings, that is permeable to a measuring fluid and/or an analyte contained in the measuring fluid, with a surface designed to be in contact with a measuring fluid, wherein the surface is designed such that, at least in a moist condition of the polymer layer obtained by moistening the surface, a contact angle of a water drop applied to the surface is less than 50°, including less than 30°, and including less than 10°.

18 Claims, 3 Drawing Sheets

(56) References Cited

U.S. PATENT DOCUMENTS

| | | |
|---|---|---|
| 2015/0038814 A1 | 2/2015 | Staib et al. |
| 2015/0068895 A1 | 3/2015 | Beriet et al. |
| 2015/0182155 A1 | 7/2015 | Bommakanti et al. |
| 2015/0216463 A1 | 8/2015 | Mao et al. |
| 2015/0257688 A1 | 9/2015 | Liu et al. |
| 2015/0323487 A1 | 11/2015 | Feldman et al. |

FOREIGN PATENT DOCUMENTS

| | | |
|---|---|---|
| CN | 103285743 A | 9/2013 |
| CN | 104458678 A | 3/2015 |
| DE | 2149183 | 4/1972 |
| DE | 2817363 A1 | 10/1979 |
| DE | 3788533 T2 | 4/1994 |
| DE | 69217315 T2 | 6/1997 |
| DE | 69514427 T2 | 8/2000 |
| DE | 19924856 A1 | 12/2000 |
| DE | 10028724 A1 | 12/2001 |
| DE | 69333400 T2 | 11/2004 |
| DE | 69434195 T2 | 12/2005 |
| DE | 60037592 T2 | 1/2009 |
| DE | 202004021824 U1 | 4/2011 |
| DE | 102011081472 A1 | 2/2013 |
| DE | 102012022894 A1 | 5/2014 |
| DE | 102014019337 A1 | 6/2015 |
| DE | 202014010579 U1 | 1/2016 |
| EP | 1591779 B1 | 11/2005 |
| GB | 1353956 A | 5/1974 |
| JP | 60125558 A | 7/1985 |

\* cited by examiner

US 10,436,738 B2

MEMBRANE AND METHOD OF MANUFACTURE

CROSS-REFERENCE TO RELATED APPLICATION

The present application is related to and claims the priority benefit of German Patent Application No. 10 2015 122 463.1, filed on Dec. 21, 2015, the entire contents of which are incorporated herein by reference.

TECHNICAL FIELD

The present disclosure concerns a membrane for a sensor, particularly an opto-chemical or electrochemical sensor, for determining a measurand dependent upon the concentration of an analyte in a measuring fluid.

BACKGROUND

Opto-chemical and electrochemical sensors frequently comprise measuring membranes that are put in contact with a measuring fluid, e.g., a measuring gas or a measuring liquid, in order to capture measured values. The measuring membranes have at least a sensor-specific function layer that has different functions, depending upon whether the sensor is an opto-chemical or an electrochemical sensor.

Many electrochemical, especially amperometric, sensors have an electrolyte chamber separated from the measuring fluid by means of a measuring membrane. The measuring membrane in amperometric sensors for determining a gas concentration in a liquid, e.g., electrochemical $O_2$, $Cl_2$, $CO_2$, $H_2S$, $NH_3$ or $SO_2$ sensors, comprises at least a function layer acting as a diffusion barrier letting the analyte diffuse from the measuring fluid into the electrolyte chamber. Such a sensor is described in, for example, DE 10 2008 039465 A1.

An opto-chemical sensor, e.g., an opto-chemical oxygen, ozone, or carbon dioxide sensor, may be based upon the principle of analyte-induced fluorescence or luminescence quenching of an organic dye—a so-called fluorophore. Opto-chemical sensors frequently comprise a sensor element featuring the measuring membrane. The sensor-specific function layer of the measuring membrane comprises the fluorophore for opto-chemical sensors. The function layer may be designed, for example, as a polymer layer in which the fluorophore is dissolved. The polymer layer is brought into contact with the measuring fluid to capture measured values. Due to interaction of the fluorophore with the analyte, the fluorescence and/or luminescence intensity of the fluorophore as a function of the analyte concentration in the measuring fluid decreases. Usually, the measuring membrane is applied to a substrate, e.g., to a glass plate or an optical fiber, to create a sensor spot.

From WO 2005/100 957 A1, we know about an opto-chemical apparatus for determining and/or monitoring an analyte contained in a fluid process medium. The known apparatus has a sensor with a measuring membrane having a porous carrier structure. A luminescent substance coming into contact with the measuring medium is embedded into the carrier structure. Furthermore, a sender and a receiver are provided, with the sender emitting measuring beams and stimulating the luminescent substance to emit luminescence radiation, and the receiver detecting the respective generated luminescence radiation. A control/evaluation unit determines the concentration and/or the partial pressure of the analyte in the measuring fluid on the basis of the quenching of the luminescence radiation of the luminescent substance.

From DE 100 51 220 A1, we know about an optical sensor for determining an analyte, especially oxygen, that mainly shows a sensor matrix consisting of a fluoro-polymer. The sensor matrix contains a luminescence indicator containing a metal complex of ruthenium, rhenium, rhodium, or iridium and at least a partially fluorinated ligand. The sensor matrix itself is designed as a film and equipped with a protective layer. The protective layer is preferably made of the same material as the sensor matrix, but does not include a luminescence indicator. Any mechanical damage to the sensor matrix is counteracted by the protective layer.

DE 10 2014 112 972 A1 describes a measuring membrane for an opto-chemical or electrochemical sensor. The measuring membrane comprises a sensor element that features at least one function layer with a sensor-specific substance and a substance material, wherein the sensor element is fully embedded into a matrix and wherein the matrix consists of a material that is accessible for the analyte at least in a partial area facing the medium and adjacent to the sensor element. The measuring membrane may be housed in a cylindrical sensor cap that is exchangeably connected with a probe body of the sensor.

In processes in the food industry or in bio-chemical or bio-technological processes, foam frequently occurs, caused by the presence of, for example, proteins. However, cleaning and disinfection procedures may also be disturbed by undesired foaming.

When the sensor is vertically installed and the measuring fluid contacting the sensor moves only with limitation, e.g., at a low stirring speed, there is frequently a problem of bubbles forming, or the accumulation of bubbles or foam on the measuring membrane. Gas bubbles clinging to the membrane may corrupt the measured values captured by the sensor. The disappearance of a gas bubble attached to a measuring membrane may, depending upon the design of the sensor, especially the above-mentioned sensor cap, take some minutes or hours.

There are various procedures aimed at preventing or suppressing the creation of foam. One option is mechanical foam destruction. A method for mechanical foam destruction is described in EP 35705 B1, in which foam is removed by a turning intake socket. This solution certainly contributes to improvement. However, since it is mostly impossible to achieve complete foam prevention, it is advisable to arrange functions directly on the sensor that prevent any foam from attaching itself to the sensor.

Often, the approach is chosen of adding substances to the measuring fluid that suppress foam generation or are meant to destroy any foam generated. However, this is not always feasible, especially if the additives might disturb the process that is to be monitored by means of the sensors.

Another option for dealing with gas bubbles that interfere with the measurement is described in U.S. Pat. No. 6,914,677 B2. In this case, it is a sensor that discovers bubbles on the sensor by detection via a second light channel. However, bubble generation is not prevented with this method.

One solution with a physical approach for preventing gas bubbles is achieved with a turbidity sensor. DE 10 2013 111416 A1 describes a turbidity sensor with an ultrasonic unit that ensures that the sensor remains bubble-free. Despite the fact that this method satisfactorily prevents the accumulation of irritating bubbles, it has the disadvantage that operating the ultrasonic unit requires additional energy, which is not always readily available for opto-chemical or electrochemical sensors.

SUMMARY

The present disclosure therefore has the objective of suggesting a membrane for an opto-electrical or electrochemical sensor, e.g., an amperometric sensor, that is designed to prevent, or at least to reduce, erroneous measurements due to the generation of foam or the accumulation of gas bubbles. This objective is achieved by the membrane according to claim 1 and a method for producing a membrane according to claim 14. Advantageous embodiments are listed in the dependent claims.

The membrane according to the present disclosure for a sensor, including an opto-chemical or electrochemical sensor, comprises a polymer layer that is permeable to a measuring liquid and/or an analyte contained in the measuring fluid, with a surface designed to be in contact with a measuring fluid, wherein the surface is designed in such a way that, at least in a moist condition of the polymer layer obtained by moistening the surface, a contact angle of a water drop applied to the surface is less than 50°, including less than 30°, and including further less than 10°.

The surface therefore is designed to be hydrophilic, at least when the polymer layer is moist, so that it is easy to moisten it with aqueous fluids. Gas bubbles do not easily attach to the hydrophilic surface in an aqueous measuring fluid, which means the surface has bubble-repellent properties.

In an embodiment, the surface in dry condition is less hydrophilic than in a moist condition obtained by moistening, in such a way that the contact angle of a water drop applied to the surface in dry condition is greater than the contact angle of a water drop applied to the surface when the polymer layer is moist.

In another embodiment, the reduction of the contact angle in a moist condition, i.e., after moistening, remains intact compared to the dry condition of the surface, even after repeated drying and moistening. Accordingly, the surface can be made hydrophilic again after drying, during which the hydrophilic properties of the surface disappear or are reduced, by the simple measure of moistening it.

The surface may be designed in such a way that it becomes super-hydrophilic after being moistened by introducing the membrane into water, for example, over a period of less than 5 minutes and over a period of less than 10 seconds, in such a way that the contact angle of a water drop applied to the super-hydrophilic surface is 0°, and wherein this super-hydrophilic condition of the surface may be reversibly re-created even after repeated drying of the surface.

In one design of the membrane, at least one function layer of the membrane is arranged on the side facing away from the surface intended for contact with the measuring medium, with said function layer comprising a sensor-specific substance, particularly a fluorophore. The sensor-specific substance may have at least one optical property that changes depending upon a concentration of an analyte in a measuring fluid interacting with the substance. The membrane may comprise at least one further layer arranged between the at least one function layer and the polymer layer. This further layer may be, for example, a colored and/or opaque layer. Any layers arranged between the polymer layer and the function layer are permeable to liquids and/or at least to the analyte.

In at least one embodiment, at least one optical property of the membrane, for example, of the polymer layer, may be modified when moistened compared to the polymer layer when dry. This enables discerning by merely optical means, such as visually, whether the membrane and/or the surface intended for contact with the measuring fluid is in hydrophilic and/or bubble-repellent condition.

In the dry condition, the polymer layer may at least transmit visible light to a lesser degree than in the moist condition, so that a layer arranged on a side of the polymer layer facing away from the surface intended for contact with the measuring medium becomes visible through the polymer layer once the surface is moistened. This further layer may, for example, be colored, so that the coloring of the layer is visually discernible through the polymer layer when the polymer layer is moist, i.e., hydrophilic. In this way, the membrane comprises a visually discernible, optical indicator showing whether the surface intended for contact with the measuring fluid has hydrophilic properties.

It has been discovered that a surface featuring one or several of the properties as described above may be obtained in a simple manner by treating the surface intended for contact with the measuring medium by energy input or a chemical reaction.

The polymer layer may comprise a halogenated, e.g., chlorinated or fluorinated, polymer, a silicon, a polymer with photo-reactive groups, a polymer with high temperature stability, including at least up to a temperature of 140° C., or a derivate of such a polymer.

In an advantageous manner, the polymer layer comprises a polymer, co-polymer, ter-polymer, or a polymer blend with adjacent and/or alternating electron withdrawing and electron pushing groups. Possible electron withdrawing groups are, for example, halogenated groups, and possible electron pushing groups are carbon-hydrogen groups, e.g., alkyl or alkene groups. In at least one embodiment, the material forming the polymer layer is crystalline or partially crystalline, which allows a visual differentiation between the layer when dry, appearing opaque, and the layer that is transparent when moist.

The polymer layer may comprise a chlorinated or fluorinated polymer with flexible groups that may be modified in an oxygen plasma in order to increase hydrophilicity in contact with water. It is advantageous to attain super-hydrophilicity in this way, i.e., a water drop applied to the modified surface of the polymer layer has a contact angle of or close to 0°. In at least one embodiment, partially halogenated polymers are groups comprising both chlorine and fluorine, including fluorinated or chlorinated groups.

For example, suitable polymers are polychlorotrifluoroethylene (PCTFE), polyhexafluoropropylene (PHFP), polyperfluoro-3-butenyl-vinyl-ether (PBVE), polyperfluoro-2,2-dimethyl-1,3 dioxole (PDD), polychlorotrifluoroethylene (PCTFE), polyperfluoropropylvinylether (PPVE), polytetrafluoroethylene (PTFE), polyvinylidenfluoride (PVDF), polyvinylfluoride (PVF), polyvinylidenfluoride (VDF), or perfluoroalkoxypolymers (PFA). Co-polymers are also suitable, e.g., a co-polymer of ethylene and CTFE (PECTFE), a co-polymer of ethylene and TFE (ETFE), a co-polymer of fluorinated ethylene and propylene (FEP), a co-polymer of TFE and PPVE (PFA), or a co-polymer of TFE and PDD (Teflon AF). Furthermore, ter-polymers are suitable, such as poly(TFE-co-HFP-co-VDF) (PTHV), a ter-polymer of vinyl fluoride, trifluorethylene, 1-chlorofluoroethylene (P(VDF-TrFE-CFE), a ter-polymer of vinyl fluoride, trifluorethylene, chlorodifluoroethylene (P(VDF, TrFE, CDFE), a ter-polymer of vinyl fluoride, trifluoroethylene, chlorotrifluoroethylene (P(VDF-TrFE-CTFE), and further variations of ter- and co-polymers comprising monomers of the polymers indicated above.

Further examples of polymers that may be rendered hydrophilic and can be used for the polymer layer are siloxanes, siloxanes with benzophenone, and long alkyl groups, i.e., alkyl groups with at least 4 carbon atoms, or a polymer blend of one polymer with benzophenone share and a polymer with a high share of alkyl. In at least one embodiment, those polymers are partially crystalline.

The treatment may comprise an ozone treatment, a plasma treatment in oxygen plasma, or irradiation with UV light. The ozone or plasma treatment may be used to render the polymer layer hydrophilic if it consists of one of the halogenated and/or partially halogenated polymers, co-polymers, or ter-polymers. A UV treatment is advantageous for rendering hydrophilic a polymer layer consisting of a polymer with photo-reactive groups, e.g., the above-mentioned siloxanes with benzophenone groups and long alkyl groups.

The material for the polymer layer is advantageously selected in such a way that the polymer layer does not feature any cyto-toxic properties.

Advantageously, the polymer layer may comprise at least partially temperature-stable fabric components such as mats, tissue, or meshes that are hydrophilic or may be rendered hydrophilic.

The polymer layer may comprise a metalloid oxide, including a metalloid oxide from the group comprising titanium oxide, zinc oxide, and silicon oxide, and/or metal nanoparticles from a metal from the group containing silver, copper, gold, and platinum. Advantageously, the metalloid oxide may be present in the form of nanoparticles in the polymer layer.

The present disclosure also comprises a sensor cap that may be removably connected with a sensor body comprising an electrical or electronic sensor switch, with the sensor cap comprising a cylindrical housing and a membrane arranged in a front end segment of the housing according to one of the embodiments described above.

The present disclosure also comprises a method for the production of a membrane for an opto-chemical or amperometric sensor, comprising provision of a membrane that has at least one polymer layer with a surface intended for contact with a measuring fluid, and treatment of the surface of the polymer layer that is intended for contact with the measuring fluid by means of energy input or by means of a chemical reaction, including by a plasma treatment or UV radiation.

The surface intended for contact with the measuring fluid may be the surface of the top layer of the membrane.

The surface of the polymer layer may be chemically treated, for example etched, by a plasma, including an oxygen plasma, or irradiated with UV radiation. It may comprise one or several of the polymer materials indicated above in the context of the description of the membrane.

In a further step, at least one second layer is applied to the side of the membrane that faces away from the treated surface, wherein the second layer is preferably optically unchangeable by the treatment of the surface of the polymer layer. The second layer may comprise a sensor-specific substance which has at least one optical property that changes depending upon a concentration of an analyte in a measuring fluid interacting with the substance.

In one variant, the sensor cap and/or the polymer layer may consist of at least one fluorinated and/or chlorinated polymer, especially one of the following materials: polyvinylentrifluorides, polytetrafluoroethylene, ethylentetrafluorethylene, polyvinylendifluorides, polyvinylidenfluorides, polychlortrifluorethylene, or a polymer blend thereof. Currently, ETFE, PFA, PVDF, and PFA are examples. The sensor cap in this case may be rendered hydrophilic by means of a plasma treatment in oxygen plasma, which means that in a moist condition of the sensor cap, a water drop applied to the membrane or the wall of the sensor cap has a contact angle of less than 30°, and preferably of 0°.

Advantageously, the material of the sensor cap, especially of a front wall onto which the membrane is mounted, and/or the material of the polymer layer of the membrane is selected in such a way that it is transparent to the measuring beam of the sensor with which the sensor cap is to be used. The measuring beam may be, for example, luminescence radiation of a sensor-specific substance contained in the membrane and/or stimulation radiation of the sensor irradiated onto the membrane through the wall from behind. The tubular wall of the cap may be blackened during manufacturing of the sensor cap in order to prevent lateral entry of radiation that might interfere with the measurement.

BRIEF DESCRIPTION OF THE DRAWINGS

Below, the present disclosure is explained in further detail on the basis of the embodiment examples shown in the illustrations. The figures show.

DETAILED DESCRIPTION

Figure 1:
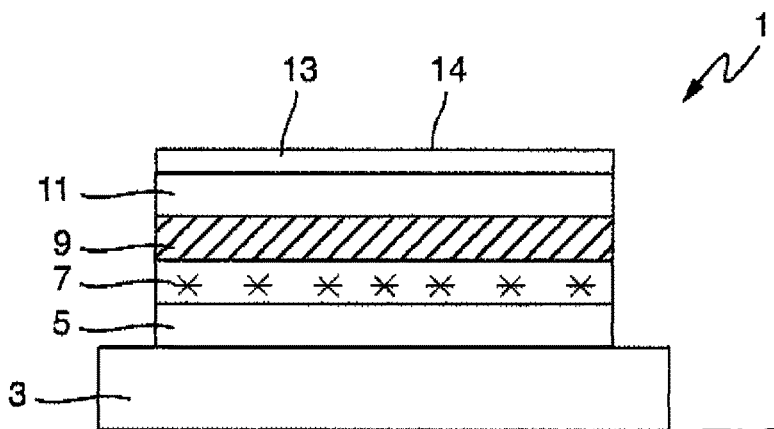
FIG. 1 shows a schematic sectional view of a bubble-repellent membrane, according to the present disclosure.

In FIG. 1, a membrane 1 for an opto-chemical sensor for determining the concentration of an analyte in a measuring fluid is schematically shown in a sectional view. The membrane 1 is affixed to a substrate 3. The substrate 3 is linked to a sensor cap that may be attached to the sensor body of an opto-chemical sensor, said sensor cap being described in more detail below. Such sensor caps and sensor bodies are known, for example, from DE 10 2014 112 972 A1 or DE 10 2011 081326 A1.

The surface 14 of the membrane 1 facing away from the substrate 3 is intended to be brought into contact with a measuring fluid, e.g., a measuring liquid or a measuring gas for conducting measurements. This surface 14 and/or a direction pointing from the substrate 3 to this surface 14 is in the following also referred to as the medium side and/or as the medium side direction. The substrate 3 may consist of a glass, e.g., quartz glass, of a ceramic, or of a plastic, for example, a polymer. Possible polymer materials for the substrate 3 are, for example, polycarbonate, cyclic olefinic co-polymers, fluorinated ethylene or propylene, polysulfones, or polyvinyl-endifluorides.

The membrane 1 comprises several layers arranged on top of one another. One of those layers is designed as a function layer 7 of the opto-chemical sensor. It comprises a sensor-specific substance, in the present embodiment, a fluorophore. The fluorophore interacts selectively with the analyte to be established in the measuring fluid in such a way that an optical property of the fluorophore changes depending upon the concentration of an analyte in the measuring fluid in contact with the membrane 1. For example, if the analyte is present, a luminescence of the fluorophore triggered by a stimulation radiation may be reduced (i.e., principle of luminescence quenching).

A darkening layer 9 is arranged on the function layer 7 side that is facing away from the substrate 3, the darkening layer 9 serving to suppress the ambient light arriving on the membrane 1 from the medium side. The function layer 7 and the darkening layer 9 may be embedded into a polymer matrix, e.g., a silicon matrix. The membrane 1 in the example shown here has a first matrix layer 5 made of silicon that is arranged between the substrate 3 and the function layer 7, and a second matrix layer 11 made of silicon that is arranged on the medium side of the darkening layer 9. In an alternative design, the function layer 7 and the darkening layer 9 may also be fully embedded into a silicon matrix.

As a final layer on the medium side, the membrane 1 has a polymer layer 13 that is intended for contact with the measuring fluid. The polymer layer 13 is preferably permeable for liquids and/or gas, so that the measuring fluid in contact with the polymer layer 13 arrives at the matrix layer 11 through the polymer layer 13. In an embodiment, the polymer layer 13 is designed so thinly that permeability to the measuring fluid is guaranteed. In an alternative embodiment, the polymer layer may have pores or larger openings that allow the measuring fluid to arrive at the lower membrane layers. The surface 14 of the polymer layer 13 on the medium side is rendered hydrophilic by energy input, e.g., by radiation and/or a chemical reaction, so that is has excellent wettability with an aqueous measuring fluid, at least when moist, and any accumulation of gas bubbles on the surface is avoided. Advantageously, the contact angle of a water drop applied to the surface when moist is smaller than 30°, for example, smaller than 10°, and for example 0°.

The treatment of the surface 14 of the polymer layer 13 may be done, for example, by treatment in oxygen plasma.

Such a plasma treatment may, for example, be done in 10 min at a microwave power of 700 W with 100 sccm oxygen. Another option for rendering the surface 14 hydrophilic is irradiation with UV radiation at an energy fluence of at least 0.1 J/cm$^2$ for 5 min with a UV lamp. Alternatively, the surface 14 may be chemically treated by the effect of an oxidation agent, e.g., ozone gas, in order to render it hydrophilic. The choice of treatment depends upon the reactivity of the material the polymer layer 13 is made of. The materials of the layers 9, 7, 5 adjacent to the polymer layer 13 on the side facing the substrate 3 are selected in such a way as to not modify their chemical and optical properties by the treatment of the polymer layer 13. In particular, the matrix layers 11, 5 should not show any aging due to the treatment.

Polymers that can be rendered hydrophilic by means of an oxygen plasma treatment and that are suitable for the polymer layer 13 are homogenized or partially halogenated polymers that comprise electron withdrawing groups, e.g., halogenated groups, and alternating electron pushing groups, e.g., hydrocarbon groups. For example, fluorinated ethylene, fluorinated propylene, polyvinylidenfluoride (PVDF), and ethylene tetrafluoroethylene (ETFE) are suitable. In at least one embodiment, the polymer material forming the polymer layer 13 is crystalline or partially crystalline.

The treatment may now be conducted on the entire surface 14 or, alternatively, only on one or several partial surfaces of the surface 14. The latter may, for example, be obtained by the use of masks. For example, masks may generate domains with different properties. The various domains may, for example, be irradiated with different radiation angles, with the hydrophilicity of the irradiated domains depending upon the radiation angle. In this way, areas with varying hydrophilicity may be created on the surface 14. Siloxanes with benzophenone and long alkyl groups with at least four carbon atoms, or polymer blends consisting of a polymer with a share of benzophenone and a polymer with a high degree of alkyl, are eligible as reactive components of the polymer layer 13 whose hydrophilicity may be modified by UV radiation.

The polymer layer 13 that has been treated in this way may show a higher degree of hydrophilicity when moist than when dry. This may, for example, become manifest in a smaller contact angle of a water drop applied to the surface 14 when the polymer layer 13 is moist, compared to the angle when dry. However, the inventors have discovered that the hydrophilic effect of the treated surface 14 does not disappear when the membrane 1 is stored in a dry condition, but instead remains permanently. As soon as a dried surface 14 is moistened again, e.g., by submerging the membrane 1 into water for a couple of seconds, the hydrophilic effect of the surface 14 is restored. It is advantageous to use a polymer as material for the polymer layer 13 that is opaque when dry, and that becomes permeable to light when moistened by water input. The polymer layer 13 that is transparent when moist makes the darkening layer 9 and/or the function layer 7 below visible, thus already allowing a visual indication of the hydrophilic status of the surface 14. This visual indication of the hydrophilic status occurs, for example, in case of the above-described plasma-treated, fluorinated or partially fluorinated, preferably crystalline or partially crystalline alkyl polymers, e.g., ETFE or PVDF.

Figure 2A:
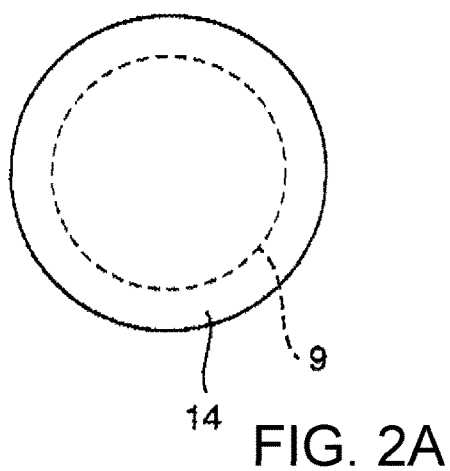
FIG. 2A shows a schematic top view of a bubble-repellent membrane shown as a sectional view in FIG. 1.
Figure 2B:
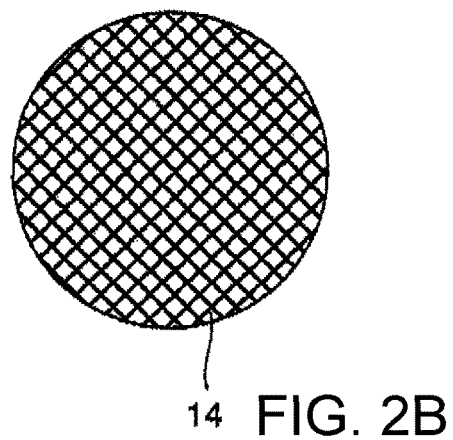
FIG. 2B shows a top view of a bubble-repellent membrane shown as a sectional view in FIG. 1 when dry.
Figure 2C:
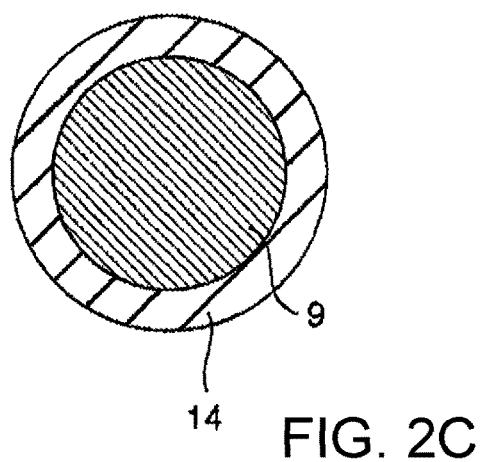
FIG. 2C shows a top view of a bubble-repellent membrane shown as a sectional view in FIG. 1 when moist.

This effect is represented schematically in FIGS. 2A-2C. FIG. 2A shows a schematic top view of the multilayer membrane 1 shown in FIG. 1. The surface 14 of the polymer layer 13 is visible from above. In dashed lines, FIG. 2A indicates the darkening layer 9 below. FIG. 2B shows a top view of the membrane 1 when dry. In this condition of the membrane 1, only the surface 14 of the opaque polymer layer 13 is visible. FIG. 2B shows a top view of the membrane 1 when moist. In this condition of the membrane 1, the polymer layer 13 is transparent, and through the polymer layer 13, one can see the darkening layer 9 below it.

This process is reversible and may be conducted repeatedly and reproduced, i.e., the polymer layer 13 becomes opaque again after drying and obtains hydrophilic properties and transparency once more after being moistened again. The membrane does not lose those properties, even after repeated drying and moistening. The membrane 1 may therefore be stored when dry without hesitation. If an immediate reaction of the sensor comprising the membrane 1 upon starting up the sensor is desired, the part of the sensor comprising the membrane 1, e.g., a sensor cap comprising the membrane 1, may be stored in a wetting cap filled with water.

As mentioned before, it is necessary that the polymer layer 13 be permeable at least to the analyte, and preferably to the measuring fluid, so that the analyte may reach the function layer 7 of the membrane 1. The polymer layer 13 may be designed porously or non-porously for this purpose, but with a small thickness. The polymer layer 13 may be designed as a continuous coating permeable to fluids.

The polymer layer 13 may be applied as a dispersion to the matrix layer 11 of the membrane 1 below.

The polymer layer 13 in one variant may comprise nanoparticles that are formed from one or several of the materials titanium oxide, zinc oxide, silicon oxide, and/or a precious metal such as gold, silver, copper, or platinum. In addition to the suppression of bubbles, dirt, and fouling/growth already attained through the hydrophilic properties of the surface 14, this also creates an additional anti-fouling effect.

The polymer layer 13 in a further variant may comprise a tissue that is formed, for example, by a plastic tissue, yarns, mats, or meshes. The tissue may be connected to and coated with metal oxides, including metal oxide nanoparticles, dyes or precious metal nanoparticles, e.g., of gold, silver, copper, or platinum. The tissue may be at least partly embedded into the matrix layer 11. The tissue may furthermore be woven together with oxidizable fibers such as carbon nano-fibers, Kevlar fibers, polyamide fibers, polyimide fibers, or fibers of polyaniline.

Figure 3:
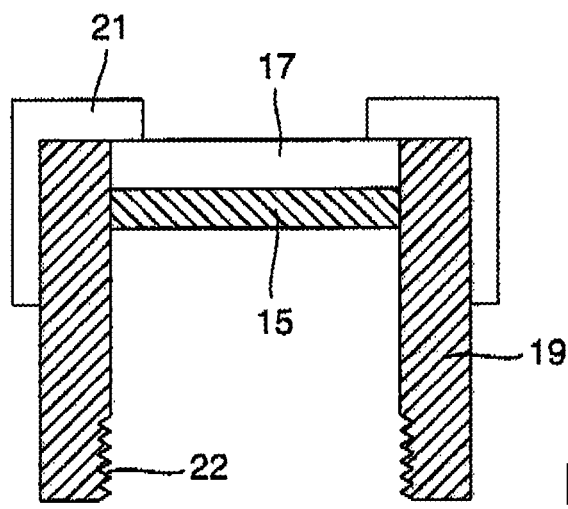
FIG. 3 shows a schematic longitudinal section representation of a first example of a sensor cap with a membrane, according to the present disclosure.

FIG. 3 represents a schematic view of a sensor cap for an opto-chemical sensor that is suitable for applications with high hygiene requirements. The sensor cap is cylindrical, represented in a longitudinal section in FIG. 3. It has a tubular housing 19 with a disk-shaped substrate 15 arranged at the front end, filling the internal cross-section of the tubular housing 19. A membrane 17 is affixed to the substrate 15, with the membrane possibly being designed like the membrane 1 schematically represented in FIG. 1. The membrane 17 closes flush and without any cap with the tubular housing 19, so that no cavities or cracks may occur in which dirt or bacteria might accumulate, or where gas bubbles may attach themselves. In addition, the sensor cap is equipped with an all-round coating 21, for example, a varnish, that protects the membrane 1 against lateral chemical attacks and that may also act as bubble and dirt repellent. Instead of a coating 21, a cap with an opening may be provided.

The sensor cap has a thread 22 on the end that is opposite the front end comprising the membrane 17, said thread serving to connect the sensor cap with a complementary thread of a sensor body (not shown). The sensor body may have a housing that can be connected to the cap, said housing containing a sensor switch suitable for capturing measured values. In the present example, the sensor is an opto-chemical sensor. It comprises a light source emitting stimulation light that stimulates a sensor-specific substance contained in the function layer of the membrane to become fluorescent. Furthermore, the sensor comprises a photo detector that receives the fluorescence radiation and generates a measuring signal that depends upon the intensity of the fluorescence radiation received. The sensor switch may serve to further process and output the measuring signal. The light source and the photo detector may be contained in the sensor body. In addition or alternatively, the sensor body may comprise light conductors that lead the stimulation light to the function layer and/or conduct radiation from the function layer to the photo detector.

Even in heavily foaming experimental approaches, no bubbles adhere to the sensor cap as shown in FIG. 3. Preferably, there is also a bubble-repellent modification provided for the surfaces of the sensor cap intended for contact with the measuring fluid in addition to the design of the sensor cap without cavities or gaps. The materials provided for the surfaces of the sensor cap in contact with the medium, especially those for the membrane 17, are, advantageously, not toxic or growth-inhibiting for microorganisms desired in the process to be monitored. Furthermore, the materials are selected in such a way that the surface in contact with the medium may be cleaned and sterilized at temperatures of up to 140° C. This allows the use of the sensor cap in bio-processes, for example, in biotechnological processes and those in food technology.

It is, furthermore, advantageous to select at least the material for those surfaces of the sensor cap that are in contact with the medium, including of the housing 19 and the coating 21, as well as the polymer layer on the side of the medium of the membrane 17, in such a way that the entire surface of the sensor cap may be rendered hydrophilic, and thus gas bubble-repellent, in the way described above for the polymer layer 13 on the side of the medium of membrane 1. Materials that are suitable for the sensor cap in this sense are thin, partially crystalline-opaque polymers such as polytetrafluoroethelene, ethylene tetrafluoroethylene (ETFE, Tefzel), polyvinylendifluorides, polyvinylidenfluorides (PVDF), polychlorotrifluoroethylene, polyethylene with ultra-high molecular weight, polyphenylene sulphide, polyimides, polybenzimidazoles, polyamidimides and their derivates, or amorphous polymers such as cyclo-olefinic co-polymers such as TOPAS, polysulphone, polycarbonate, polyphenylene ether, polyethyleneimine, polyethersulfones, polyphenylsulfones, polysulfones Hyflon AD 60/80, Teflon AF 1600/2400 and their derivates. It is advantageous to use such polymer materials, including as materials for the substrate 15, that are transparent from the start for the stimulation radiation radiating from behind through the substrate onto the membrane 1 and for the measuring beam generated in the function layer 7. The sensor cap 19 may consist of the same material as the substrate 15, with the wall of the housing 19 being coated with a non-transparent material, e.g., blackened, in case the sensor cap 19 is used with an opto-chemical sensor.

Figure 4:
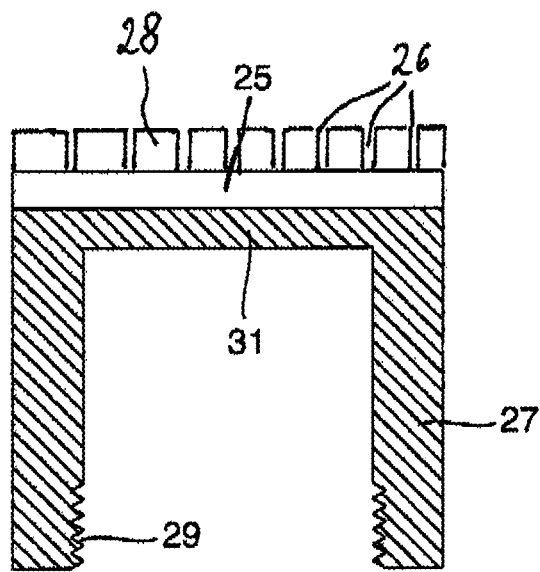
FIG. 4 shows a schematic longitudinal section representation of a second example of a sensor cap with a membrane, according to the present disclosure.

FIG. 4 shows another example embodiment for a sensor cap of an opto-chemical sensor in a schematic longitudinal section view. Analogously to the sensor cap shown in FIG. 3, the sensor cap shown in FIG. 4 is designed to be connected with a sensor body that comprises the further sensor components such as a measuring arrangement and/or a radiation source and a photo detector, as well as possibly a light conductor. The sensor cap is designed as a cylinder and has a tubular housing wall 27 that is closed by a disk-shaped wall 31 at the front. The wall 31 and the wall 27 are designed as one piece in the present example. On the end of the sensor cap that is opposite wall 31, there is an internal thread 29 that may be connected to a complementary thread of the sensor body (not shown). The wall 31 serves as a substrate onto which a membrane 25 is affixed, wherein the latter may be designed in several layers. Just like the membrane 1 shown in FIG. 1, the membrane 25 may comprise a function layer embedded into a silicon matrix, with a darkening layer possibly arranged on the medium side of the function layer. This variant is particularly suitable for simply designed, cost-effective sensors which may, for example, be used in less chemically aggressive conditions, e.g., on fish farms or in aquariums.

A polymer layer 28 with pores 26 is arranged on the membrane 25. The polymer layer 28 and the material of the housing 27 are corrosion-resistant and hydrolitically stable in sterilization cycles up to 140° C. The measuring fluid including the analyte may reach the membrane 25 through the pores 26. Alternatively, a film may be applied to the membrane 25 that is permeable at least to the analyte.

In this case, the sensor cap may be made of an optically transparent material that simultaneously serves as a substrate, such as polycarbonate, cyclic olefinic co-polymers, fluorinated ethylene, fluorinated propylene, polysulfones, or polyvinylendifluorides.

The entire surface of the sensor cap intended for contact with the measuring fluid, i.e., the surface of the membrane in contact with the medium and the outer surfaces of the housing 27, as well as the polymer layer 28, may be rendered hydrophilic, and thus bubble-repellent, by a treatment, e.g., a plasma treatment as described above. The materials of the sensor caps, especially the housing material and the polymer layer 28 in contact with the media, may be selected, as described before for the polymer layer 13 of the membrane 1 represented in FIG. 1, in such a way that they are transparent when moist, but opaque in a dry—and thus less hydrophilic—condition, in order to allow users to visually recognize the hydrophilicity of the respective surfaces. Suitable materials for the substrate, the cap, and the polymer layer 28 are, for example, the other fluorinated or partially fluorinated alkyl-polymers mentioned above.

The example embodiments shown in FIGS. 1-4 represent a membrane and sensor caps for opto-chemical sensors based upon the principle of luminescence quenching. Similarly, in a very similar way to that described by means of FIGS. 1-4, it is possible to render membranes and/or sensor caps of other sensor types hydrophilic and design them hygienically. Membranes of amperometric sensors have one or several function layers through which the analyte selectively may diffuse into an electrolyte space arranged behind the function layer. This is described, for example, in DE 10 2008 039465 A1. A surface of such a membrane of an amperometric sensor in contact with a medium may be designed in the same way as a hydrophilic polymer layer that is permeable to the analyte and/or the measuring fluid, such as the surface 14 of membrane 1 in FIG. 1 in contact with the medium. Similarly, the present disclosure described here may also be applied to optical sensors working on the basis of a colorimetric measuring principle.

In the following, examples for the production of sensor caps with hydrophilic properties are described:

Example 1: Hydrophilization by Plasma Treatment

Firstly, a silicon layer is applied as a matrix layer to a porous PVDF membrane, using methods known to the person skilled in the art such as blanket coating, electrospinning, spraying, spray coating, or dip coating. After the respective waiting time, an opaque darkening layer, and eventually, the function layer, is applied, comprising a sensor-specific substance, e.g., a substance reacting selectively to the analyte by modifying an optical property. The membrane is hardened and then glued to a substrate. The sensor spot manufactured in this way is then united with a sensor cap and treated with oxygen plasma in a plasma oven for 10 min at a microwave power of 700 W at 100 sccm oxygen. The finished sensor cap may be equipped with a protective film or protective cap when dry, or with a wetting cap for moist storage.

Example 2: Hydrophilization by UV Radiation

A layer of silicon is first applied to a polyimide film consisting of a polyimide polymer with a main chain and side chains, such as an alkyl or perfluoroalkyl groups with a length of more than four carbon atoms and benzophenone elements in the main chain, using a method known to the person skilled in the art. After the respective waiting time, an opaque darkening layer, and eventually, the function layer comprising a sensor-specific substance, is applied. The resulting membrane is hardened and then glued to a substrate. The resulting sensor spot is then united with a sensor cap. The cap manufactured in this way is irradiated for 15 seconds (sec) with the light from a UV lamp having a fluence of 0.5 J/cm$^2$.

Example 3: Hydrophilization by UV Radiation and Structuring

A layer of silicon is first applied to a polyimide film consisting of a polyimide polymer with a main chain and side chains, such as an alkyl or perfluoroalkyl groups with a length of at least four carbon atoms and benzophenone elements in the main chain, using a method known to the person skilled in the art. After the respective waiting time, an opaque darkening layer, and eventually, the function layer, is applied. The membrane is hardened and then glued to a substrate. The resulting sensor spot is then united with a sensor cap. The sensor cap manufactured in this way is irradiated for 15 sec with the light from a UV lamp and a mask at an angle of 45° to the vertical with a fluence of 0.5 J/cm$^2$.

Example 4: Membrane with Incorporated Substance to be Rendered Hydrophilic

Carbon fibers are woven into/interlaced with a porous, chemically stable membrane. First, a silicon layer is applied to the resulting composite membrane by methods known to the person skilled in the art. After the respective waiting time, an opaque darkening layer, and eventually, the function layer with a sensor-specific substance, is applied. The membrane is hardened and then glued to a substrate. The resulting sensor spot is then united with the sensor cap. The membrane is placed into a strongly oxidizing medium and thus rendered hydrophilic.

In the following, some measurements are described and measuring results presented that are the outcome of using a sensor spot manufactured as described in Example 1.

1. Bubble Tests

Bubble tests were conducted in which a planar cap manufactured according to Example 1 above and featuring a membrane affixed to a glass substrate and rendered hydrophilic by means of plasma treatment in oxygen plasma is positioned in an aqueous solution and exposed to a current of gas bubbles. It was observed that the membrane remained free of bubbles. The gas bubbles immediately ran off the surface of the membrane in contact with the medium. Comparative tests with a membrane that had a hydrophobic silicon coating in contact with the medium did not demonstrate such a bubble-repellent effect.

2. Contact Angle Measurement

Contact angle measurements of a water drop were conducted on the surface of a sensor spot (labeled "Special Membrane") manufactured as described in Example 1 and rendered hydrophilic by means of the plasma treatment described there, wherein said surface is intended for contact with the measuring fluid. Comparative measurements were conducted with a conventional sensor spot (labeled "Silicon Membrane"). The conventional sensor spot comprises a silicon matrix surrounding the function layer. The surface of the conventional sensor spot intended for contact with the measuring fluid is a surface of the silicon matrix. Table 1 summarizes the measuring results.

TABLE 1

Measuring Results

| Time | Special Membrane | Silicon Membrane |
|---|---|---|
| 0 | 35° | 90° |
| 1 s | 30° | 90° |
| 5 s | 30° | 90° |
| 60 s | 0° | 90° |
| 30 d | 0° | 90° |
| 90 d | 0° | 90° |

It is evident that the contact angle on the Special Membrane is 35° at the start and decreases to 0° after 60 seconds, during which the Special Membrane is moistened. Hence, the surface of the Special Membrane is already more hydrophilic when dry than the surface of the Silicon Membrane used for comparison, for which the contact angle remains constantly 90°. The two last measured values of the contact angle were determined after 30 days and after 90 days of dry storage. It becomes evident that the Special Membrane retains its hydrophilic properties even after 90 days, and/or regains them upon contact with water. The process of hydrophilization when moistening a dried membrane with water takes only a few seconds, even after dry storage over a period of 3 months.

3. Reaction Time

Measurements of the oxygen concentration in a measuring gas were conducted by means of an opto-chemical sensor based upon the principle of fluorescence quenching, wherein the opto-chemical sensor was equipped with a sensor cap for capturing a first series of measured values that comprised a sensor spot (Special Membrane) manufactured and rendered hydrophilic by means of the method described in Example 1. In order to capture a comparative series of measured values, the sensor was equipped with a sensor cap comprising a conventional membrane (Silicon Membrane) with a silicon matrix surrounding the function layer.

Figure 5:
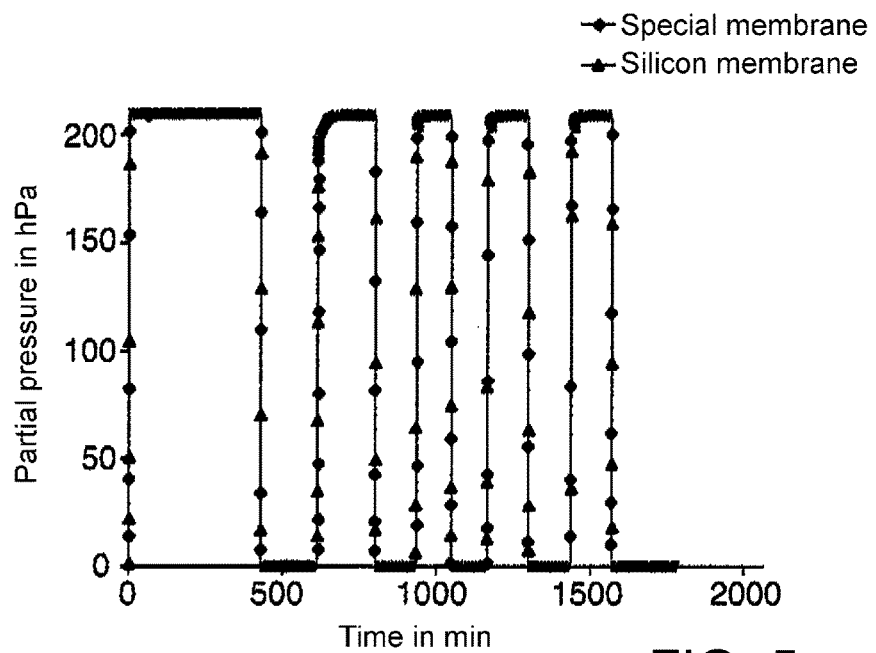
FIG. 5 shows a plot of measuring signals as a function of time of an opto-chemical oxygen sensor with a conventional membrane and of the opto-chemical oxygen sensor with a membrane according to the present disclosure.

The area of the sensor comprising the sensor cap and intended for contact with the measuring medium was alternately exposed to oxygen-free nitrogen and to air as the measuring gas. The partial oxygen pressure captured is entered as a function of time in FIG. 5. It is evident that the sensor spot (Special Membrane) manufactured according to the present disclosure has comparably fast reaction times compared with the conventional sensor spot. Hydrophilization of the membrane thus does not affect the sensor reaction time.

4. Changes in the Measuring Values by Hydrophilization

Figure 6:
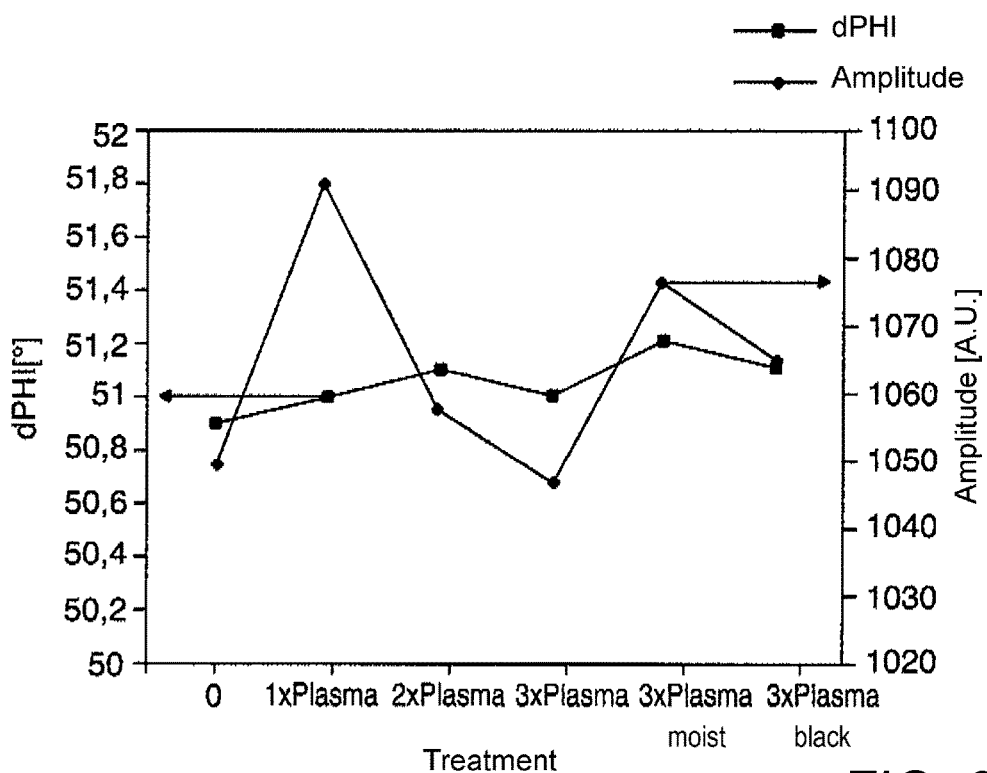
FIG. 6 shows a plot of measuring signals of an opto-chemical oxygen sensor according to the present disclosure after several treatment steps of the surface of the membrane of the sensor that is in contact with the measuring fluid.

FIG. 6 shows the measured values of the changes of the phase angle dPhi and the amplitude of the measuring signal of an opto-chemical oxygen sensor working with the principle of fluorescence quenching whose sensor membrane was subjected to different pre-treatments. The sensor membrane has a structure analogous to that of the membrane 1 represented in FIG. 1. The polymer layer of the membrane in contact with the medium is made of PVDF in the present example embodiment. The treatment steps conducted before the measured value was captured are illustrated on the x-axis of the diagram shown in FIG. 6. All the measured values were captured in air as the measuring fluid.

The individual measuring values are now explained in the sequence as shown in the diagram from left to right along the x-axis. The first measured values from the left (abscissa value "0") were captured in air with the untreated sensor membrane, i.e., the polymer layer of the membrane in contact with the medium had not yet undergone any treatment. The second measured values (abscissa value "1×plasma") were captured after a one-time plasma treatment of the surface of the measured value in contact with the medium in oxygen plasma, with the membrane being dry and the measurement conducted in air. The plasma treatment was done over a period of 10 min at a microwave power of 700 W with 100 sccm oxygen. The third series of measuring values ("2×plasma") was obtained after a double plasma treatment of the surface of the membrane on the side of the medium over a period of 10 min each with the parameters as set out above in oxygen plasma, with the membrane being dry and the measurement conducted in air. The fourth series of measured values ("3×plasma") was obtained once more in air, after a triple plasma treatment over a period of 10 min each with the parameters as set out above. The fifth series of measuring values ("3×plasma, moist") was obtained after a triple plasma treatment followed by moistening the membrane, with the measured values being captured immediately after moistening. The final series of measured values ("3×plasma, black") was measured in air after a waiting time of 30 s after the polymer layer of the membrane in contact with the medium had become transparent when moist, and the black darkening layer below had become visible.

As shown, the measured values varied only to a small degree, in the range of the measurement error. The treatment for hydrophilization of the membrane therefore only has a small influence, usually negligible, on the measuring properties of the sensor. Even the chemical modification of the polymer layer that leads to the polymer layer becoming transparent (i.e., last series of measured values) does not influence the measurement. The sensor performance is, on the contrary, significantly enhanced by the prevention of bubble accumulations and the simultaneous anti-fouling effect due to hydrophilization.

The invention claimed is:

1. A membrane for an opto-chemical sensor, comprising:
 a polymer layer having pores or openings and a surface embodied to contact a measuring fluid, the polymer layer permeable to the measuring fluid and/or an analyte contained in the measuring fluid, wherein the surface is further embodied such that, at least in a moist condition of the polymer layer, upon moistening the surface a contact angle of a water drop in contact with the surface is less than 50°;
 a silicon matrix layer arranged on a side of the polymer layer opposite the surface; and
 at least one function layer disposed on a side of the polymer layer opposite the surface embodied to contact the measuring medium, wherein said function layer comprises a sensor-specific substance.

2. The membrane according to claim 1, wherein the surface in a dry condition is less hydrophilic than in the moist condition such that the contact angle of a water drop in contact with the surface in the dry condition is greater than the contact angle of a water drop in contact with the surface in the moist condition.

3. The membrane according to claim 2, wherein the decrease of the contact angle in the moist condition relative to the dry condition is reversible and remains functional after repeated drying and wetting of the surface.

4. The membrane according to claim 3, wherein the surface becomes super-hydrophilic, such that the contact angle of a water drop in contact with the surface is approximately 0°, after being moistened by introducing the membrane into water over a period of less than 5 minutes.

5. The membrane according to claim 1, wherein the sensor-specific substance is a fluorophore.

6. The membrane according to claim 1, wherein the silicon matrix layer is arranged between the at least one function layer and the polymer layer.

7. The membrane according to claim 1, wherein the polymer layer in the dry condition at least transmits visible light to a lesser degree than in the moist condition, such that a layer disposed on a side of the polymer layer opposite the surface embodied to contact the measuring medium becomes visible through the polymer layer once the surface is moistened.

8. The membrane according to claim 1, wherein the surface embodied to contact the measuring medium is treated by energy input and/or a chemical reaction.

9. The membrane according to claim 1, wherein the polymer layer comprises a silicon, a polymer with photoreactive groups, a polymer with high temperature stability at least up to a temperature of 140° C., or a derivate of such a polymer.

10. The membrane according to claim 1, wherein the polymer layer comprises a polymer, a co-polymer, a terpolymer, or a polymer blend with adjacent or alternating electron withdrawing groups and electron pushing groups.

11. The membrane according to claim 10, wherein the electron withdrawing groups include halogenated groups and the electron pushing groups include carbon-hydrogen groups.

12. The membrane according to claim 1, wherein the polymer layer comprises a metalloid oxide from a group consisting titanium oxide, zinc oxide, and silicon oxide, and/or metal nanoparticles of a metal from a group consisting of silver, gold, and platinum.

13. The membrane according to claim 1, wherein contact angle of a water drop in contact with the surface is less than 10° or less than 30°.

14. A method for production of a membrane for an opto-chemical or electrochemical sensor, comprising:
    providing the membrane including at least one polymer layer with a surface embodied to contact a measuring fluid, the polymer layer being permeable to the measuring fluid and/or an analyte contained in the measuring fluid;
    providing a function layer arranged on a side of the polymer layer opposite the surface and including a sensor-specific substance;
    providing a silicon matrix layer between the polymer layer and the function layer; and
    treating the surface by means of energy input and/or by means of a chemical reaction such that, at least in a moist condition of the polymer layer, upon moistening the surface a contact angle of a water drop in contact with the surface is less than 50°.

15. The method of claim 14, wherein the treating includes etching by a plasma, etching by an oxygen plasma, or irradiation with UV radiation.

16. The method according to claim 14, the method further comprising applying at least one second layer to a side of the membrane opposite the treated surface, wherein the second layer is optically unchangeable by the treating of the surface of the polymer layer.

17. The method according to claim 16, wherein the at least one second layer includes a fluorophore substance having at least one optical property that changes depending upon a concentration of an analyte in a measuring fluid interacting with the substance.

18. An opto-chemical sensor, comprising:
    a membrane including:
        a polymer layer having pores or openings and a surface embodied to contact a measuring fluid;
        a function layer including a fluorophore, the function layer arranged on a side of the polymer layer opposite the surface; and
        a silicon matrix layer arranged between the polymer layer and the function layer, at least one of the polymer layer and the function layer being embedded into the silicon matrix layer;
    wherein the polymer is permeable to the measuring fluid and/or an analyte contained in the measuring fluid, wherein the surface is embodied such that, at least in a moist condition of the polymer layer upon moistening the surface, a contact angle of a water drop in contact with the surface is less than 50°;
    wherein, during use of the opto-chemical sensor, an optical property of the fluorophore changes based on a concentration of an analyte in the measuring fluid interacting with the fluorophore.

* * * * *